(12) United States Patent
Park

(10) Patent No.: US 10,098,388 B2
(45) Date of Patent: Oct. 16, 2018

(54) ABDOMEN WEAR

(71) Applicant: Suy Ik Park, Seoul (KR)

(72) Inventor: Suy Ik Park, Seoul (KR)

( * ) Notice: Subject to any disclaimer, the term of this patent is extended or adjusted under 35 U.S.C. 154(b) by 54 days.

(21) Appl. No.: 15/317,207

(22) PCT Filed: Jun. 8, 2015

(86) PCT No.: PCT/KR2015/005693
§ 371 (c)(1),
(2) Date: Dec. 8, 2016

(87) PCT Pub. No.: WO2015/190766
PCT Pub. Date: Dec. 17, 2015

(65) Prior Publication Data
US 2017/0105457 A1    Apr. 20, 2017

(30) Foreign Application Priority Data
Jun. 8, 2015    (KR) .................. 10-2014-0069794

(51) Int. Cl.
*A41B 9/00*    (2006.01)
*A41B 9/06*    (2006.01)
(Continued)

(52) U.S. Cl.
CPC .............. *A41B 9/008* (2013.01); *A41B 9/06* (2013.01); *A41D 1/22* (2013.01); *A61F 13/14* (2013.01);
(Continued)

(58) Field of Classification Search
CPC ............ A41D 13/0525; A41D 2400/10; A41D 23/00; A41D 2023/004; A41D 2300/30;
(Continued)

(56) References Cited

U.S. PATENT DOCUMENTS 1,359,346 A * 11/1920 Fields ................... A61F 5/24
                                                                                  450/154
1,403,974 A *  1/1922 Norman ................ A41F 9/025
                                                                                  2/309
(Continued)

FOREIGN PATENT DOCUMENTS

KR    2003497860000    4/2004
KR    2004515090000   12/2010
KR       20130090819    8/2013

OTHER PUBLICATIONS

English language machine translation of KR 20130090819 (Pub. Aug. 2013), 15 pages.*

(Continued)

*Primary Examiner* — Amy Vanatta
(74) *Attorney, Agent, or Firm* — IPLA P.A.; James E. Bame

(57) ABSTRACT

An abdomen wear includes a front cover part (20) formed by cutting a single-layered, and particularly a two-layered knit on bias to cover an abdomen of a body; ends (21) of the front cover part, a seam part (22) of both ends, and left and right button parts (23) to cause the front cover part to come into close contact with the abdomen; a binding part (33) including a detachable part (30) having an elastic ring (32) on which a tie adjusting part (31) is formed, the tie adjusting part being adjustable in a tie; and an upper elastic ring (41) having a button or a snap (29) on an upper-end central portion (40) of the front cover part or a seam part (40*a*) of the upper-end central portion.

5 Claims, 4 Drawing Sheets

(51) Int. Cl.
*A61F 13/14* (2006.01)
*A41D 1/22* (2018.01)

(52) U.S. Cl.
CPC ....... *A41B 2400/32* (2013.01); *A41B 2500/10* (2013.01)

(58) Field of Classification Search
CPC .......... A41D 2300/326; A41D 2300/33; A41D 2300/332; A41D 1/22; A41D 1/21; A41D 13/0506; A41D 13/0537; A41D 13/055; A41D 13/0556; A41D 13/0562; A41D 13/0568; A41D 13/0575; A41D 27/04; A41D 27/12; A41B 9/008; A41B 9/14; A41B 2300/332; A41B 9/00; A41B 9/06; A41B 1/10; A41B 1/18; A41B 2400/32; A41B 2500/10; A41C 1/08; A61F 13/14; A41F 9/00; A41F 9/002; A41F 9/02; A41F 1/02; A41F 1/00
USPC .............................................. 2/338, 464, 52
See application file for complete search history.

(56) References Cited

U.S. PATENT DOCUMENTS

| | | | | | |
|---|---|---|---|---|---|
| 2,297,955 | A | * | 10/1942 | Greene | A41C 1/08 2/315 |
| 2,563,956 | A | * | 8/1951 | Pietrowicz | A41D 13/04 2/464 |
| 2,671,222 | A | * | 3/1954 | Hochberg | A41F 5/00 2/229 |
| 3,094,990 | A | * | 6/1963 | Neilson | A41B 9/002 2/400 |
| 2011/0265240 | A1 | * | 11/2011 | Frey | A41B 9/06 2/69 |
| 2011/0296591 | A1 | * | 12/2011 | Park | A41B 9/00 2/401 |

OTHER PUBLICATIONS

English language machine translation of KR 200349786 (Pub. Apr. 2004), 14 pages.*

* cited by examiner

ABDOMEN WEAR

BACKGROUND

The present invention relates to an abdomen wear, and more particularly, to an abdomen wear, in which button parts are provided on both ends or seam parts of both ends of a front cover part formed by cutting a single-layered, and particularly a two-layered knit on bias to cover an abdomen of a body, openings are formed in portions of left and right sides to form the shape of a pocket or a pocket is provided to be opened or closed using a zipper provided on a front, so that it is convenient to put or take a separate liner into or out from the pocket via the openings or the zipper, a detachable part is provided to have an elastic ring on which a tie adjusting part is formed to adjust a ring for easily binding the front cover part and the detachable part in a tie, a button or a snap is provided on an upper-end central portion of the front cover part or a seam part of the upper-end central portion, and an upper elastic ring similar to the detachable part is provided, so that it is convenient for a user to put on the abdomen wear while effectively keeping the abdomen warm.

As well known to people, a person's abdomen should be always kept warm to aid in blood circulation, promote digestion, absorption and evacuation, guarantee a good sleep, allow for abdominal respiration, maintain and rise a body temperature and consequently promote health. However, since people usually live or sleep without wearing upper clothing in summer, the abdomen is exposed to an outside for a lengthy period of time and people are likely to have a pain in the stomach. Further, when people work long hours in an air-conditioned office, the body temperature is suddenly lowered, so that they frequently suffer from a cold, cough, and a stomachache. Since it is difficult to keep the abdomen warm in spring, autumn, change of seasons, and cold winter, it frequently damages health.

Accordingly, in order to keep the abdomen warm, Korean Patent No. 10-1402420 has been proposed, which is entitled "abdomen wear". The abdomen wear is intended to always maintain a fixed position without moving after a user puts on the abdomen wear. However, the abdomen wear is problematic in that an adjusting part undesirably protrudes in a detachable part, it is required to easily detachably attach the detachable part, improve performance after a user puts on the abdomen wear, improve a structure of separating an elastic ring of an upper end, improve the availability of a single-layered front cover part, and improve the heat insulating effect, aesthetic effect, adhesion, elasticity, and wearability of the abdomen wear.

SUMMARY OF THE INVENTION

An embodiment of the present invention is directed to an abdomen wear, in which left and right button parts are provided on both ends or seam parts of both ends of a front cover part formed by cutting a single-layered, and particularly a two-layered knit on bias to cover an abdomen of a body, openings are formed in portions of left and right sides to form the shape of a pocket therein or a pocket is provided to be opened or closed using a zipper provided on a central portion of a front, so that it is convenient to put or take a separate liner into or out from the pocket via the openings or the zipper, a detachable part is provided to have an elastic ring on which a tie adjusting part is formed to adjust a ring for easily binding the front cover part and the detachable part in a tie, lengths of the front cover part and the detachable part are adjusted, a button or a snap is provided on an upper-end central portion of the front cover part or a seam part of the upper-end central portion, and an upper elastic ring having a structure and a function similar to those of the detachable part is provided, so that it is convenient for a user to put on the abdomen wear while effectively keeping the abdomen warm.

According to an aspect of the present invention, there is provided an abdomen wear including a front cover part 20 formed by cutting a single-layered, and particularly a two-layered knit on bias to cover an abdomen of a body; both ends 21 of the front cover part, seam parts 22 of both ends, and left and right button parts 23 to cause the front cover part to come into close contact with the abdomen of the body; a binding part 33 including a detachable part 30 having an elastic ring 32 on which a tie adjusting part 31 is formed, the tie adjusting part being adjustable in a tie; and an upper elastic ring 41 having a button or a snap 29 on an upper-end central portion 40 of the front cover part or a seam part 40a of the upper-end central portion, and having a configuration and a function similar to those of the detachable part 30.

According to another aspect of the present invention, openings 26 may be provided on portions of left and right sides of the front cover part 20 formed in two layers, thus forming 26a a pocket shape therein, or a zipper 27 may be provided on a central portion of a front of the front cover part, thus forming a pocket 27b, and a liner attachment 50 may be formed on a surface therein to allow a separate liner 51 to be attached thereto.

According to a further aspect of the present invention, the front cover part 20 and the detachable part 30 may be located at an intermediate position of an entire waist circumference to cover a half or less of the entire waist circumference and a half or more thereof, respectively.

According to still another aspect of the present invention, the separate liner 51 may be further provided inside the front cover part, the attached separate liner 51 may be selected from a group including padded wormwood cotton, padded cotton (mugwort, medicinal herb, herb, vegetable, silk, wool), fiber, and leather, and an attachment 55 of the separate liner may further include a Velcro® tape (hook-and-look fastener) hook 52 and a Velcro® tape (hook-and-look fastener) auxiliary part 53.

According to yet another aspect of the present invention, the front cover part, the both ends 21, seam parts of the both ends and an upper end, and a predetermined portion and an edge of the separate liner 51 may further include various auxiliary parts 28, such as lace, bias, patch or decoration, so as to improve aesthetic effect, adhesion and elasticity.

According to another aspect of the present invention, the front cover part may further include on a lower portion thereof: a lower elastic ring provided on a lower-end central portion or a seam part of the lower-end central portion, and having a button; or a lower extension directly or indirectly extending a lower end downwards.

According to the present invention, the abdomen wear is advantageous in that the front cover part formed in a single layer to cover the abdomen of the body is put on as underwear or outer clothing mainly in summer to keep the abdomen warm, and the front cover part 20 formed by cutting the two-layered knit on the bias has on portions of left and right sides thereof the openings 26 to form 26a the pocket shape, the pocket 27b is provided to be opened or closed by the zipper 27 provided on the central portion of the front thereof, so that it is convenient to put or take the separate liner 51 into or out from the pocket, and the liner attachment 50 is formed on a surface of the lining 24 of the front cover part.

Further, the abdomen wear is advantageous in that both ends 21 of the front cover part, the seam parts 22 of both ends, and the left and right button parts 23 are provided to cause the front cover part to comfortably come into close contact with the abdomen of the body, the binding part 33 including the detachable part 30 having the elastic ring 32 on which the tie adjusting part 31 is formed is provided, the tie adjusting part being adjustable in the tie, and the upper elastic ring 41 having the button or the snap 29 on the upper-end central portion 40 of the front cover part or the seam part 40a of the upper-end central portion, and having a configuration and a function similar to those of the detachable part 30 is provided, so that it is convenient for a user to put on the abdomen wear.

Further, the size of the front cover part and the length of the detachable part may be adjusted, so that the front cover part and the detachable part may be located on a front region and a back region of the waist at an intermediate position of the waist, respectively, to be fit for a user's abdomen and waist. The detachable part 30 is adjusted by the tie adjusting part 31, so that the abdomen wear does not stimulate the back or sides even when a user takes an exercise in a supine position, thus solving problems of inconvenience after he or she puts on the abdomen wear.

Further, the abdomen wear according to the present invention is advantageous in that it keeps a user's abdomen warm for 24 hours, thus aiding in blood circulation, promoting digestion, absorption and evacuation, guaranteeing a good sleep, allowing for abdominal respiration, maintaining and rising a body temperature and thereby being beneficial to health. This may slightly help to save energy for heating and cooling, and may be used as an emergency mask when smoke or gas is produced in the event of a fire or a disaster, and may be easily washed by a washing machine.

Furthermore, the abdomen wear according to the present invention is advantageous in that it may be used to keep the abdomen warm regardless of age or sex, and the separate liner 51 may be used to more effectively keep the abdomen warm.

DETAILED DESCRIPTION OF THE INVENTION

Figure 1A:
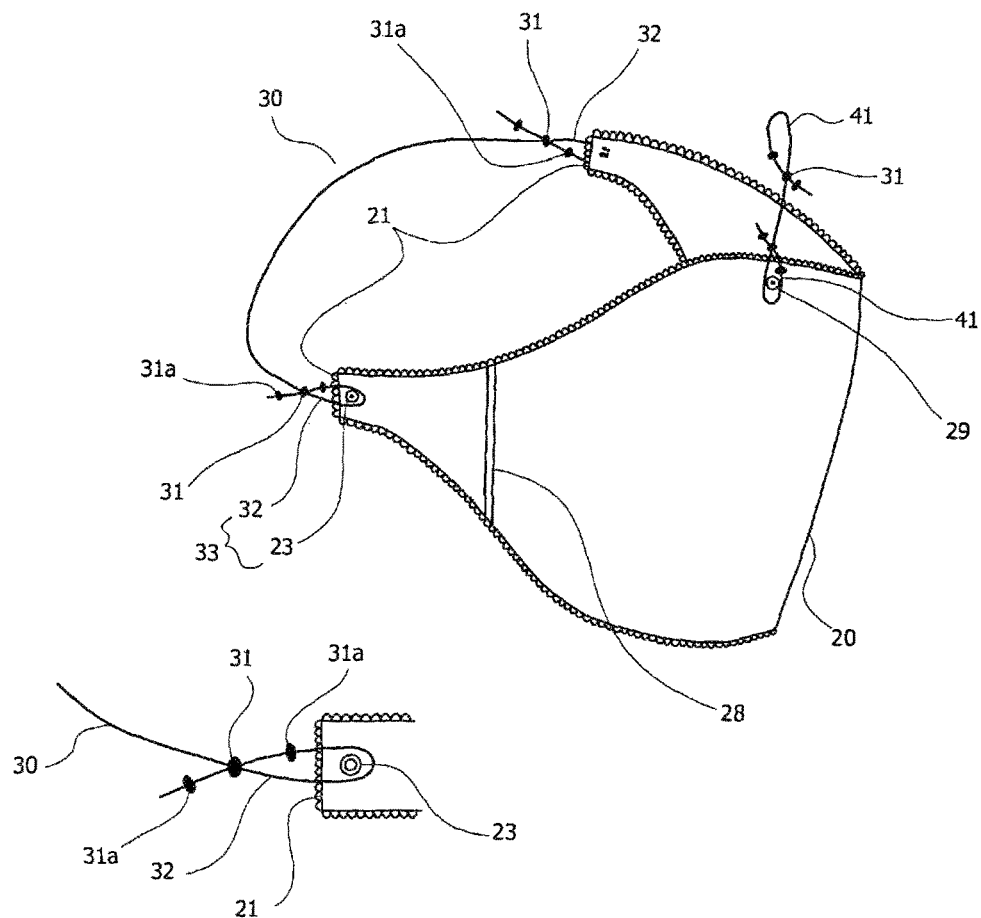
FIGS. 1A to 1C are a perspective view (FIG. 1A) illustrating a first abdomen wear according to an embodiment of the present invention, and a front view (FIG. 1B) and a rear view (FIG. 1C) of a front cover part.

Exemplary embodiments of the present invention will be described below in more detail with reference to the accompanying drawings so that this disclosure will be thorough and complete and will fully convey the scope of the present invention to those skilled in the art. Hereinafter, preferred embodiments of the present invention will be described in detail with reference to the accompanying drawings. Throughout the disclosure, like reference numerals refer to like parts throughout the various figures and embodiments of the present invention.

Figure 1B:
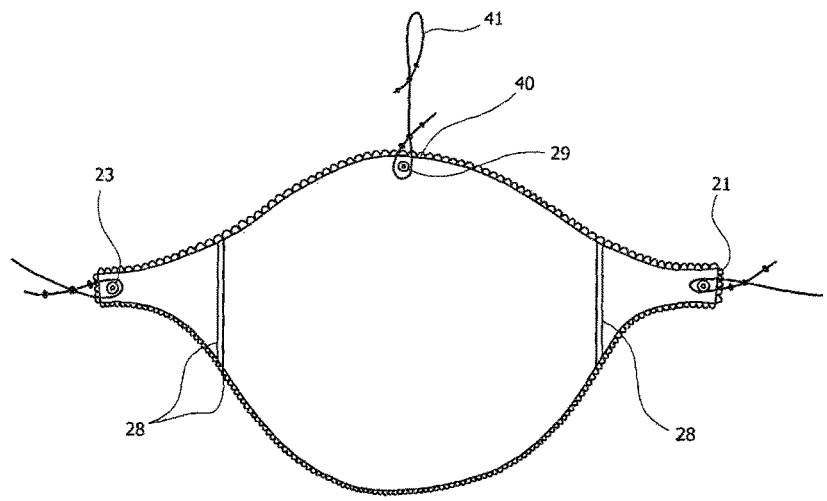
Figure 1C:
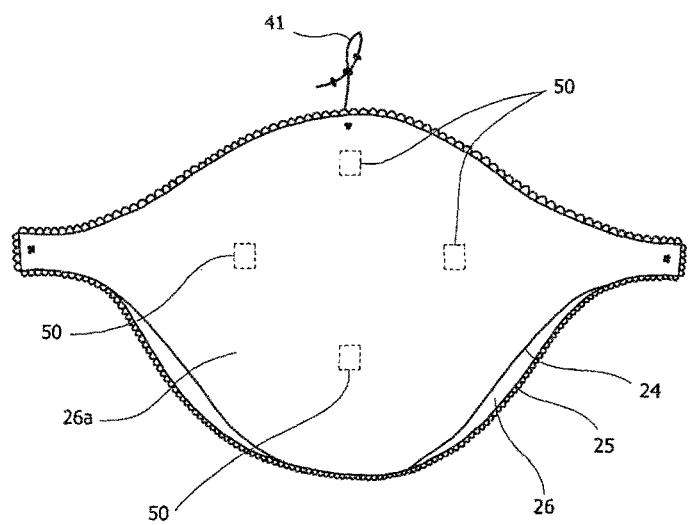

Referring to FIGS. 1A to 1C, a front cover part 20 may cover the abdomen of a body to keep the abdomen warm, and both ends 21 of the front cover part 20 may extend slightly long to the left and right to cover a portion of a back region of the waist. That is, in FIGS. 1A to 1C, the length of the front cover part 20 may be set to cover ½ or more, preferably about ⅔ of the entire waist circumference. Thus, a detachable part 30 included in a binding part 33 may cover ½ or less, preferably about ⅓ of the entire waist circumference.

Referring to FIG. 1A that is a perspective view of the abdomen wear according to the first embodiment, the abdomen wear has the front cover part 20, both ends 21, left and right button parts 23, the binding part 33, the detachable part 30, an elastic ring 32, a button (or snap) 29 of an upper-end central portion, and an upper elastic ring 41.

The front cover part 20 may be vertically inclined to correspond to the abdomen and thereby cover the abdomen, and both ends 21 of the front cover part may extend slightly long to cover a middle portion of the waist or a portion of the back region of the waist. Patches serving as one of various auxiliary parts 28 are vertically formed on left and right sides near to both ends of the front cover part. Since the front cover part is formed by cutting mainly a two-layered knit on the bias, the patch serves to mitigate the elasticity of the knit mainly using textile, in addition to enhancing the aesthetic effect of design.

The left and right button parts 23 are provided on the both ends 21 of the front cover part. Each of the left and right button parts 23 allows the front cover part 20 and the elastic ring 32 of the detachable part 30 to be connected to each other via the binding part 33, thus preventing undesirable removal. The elastic ring 32 of the detachable part 30 allows the front cover part to come into close contact with the abdomen. The button (snap) 29 is provided on a central portion of an upper end of the front cover part, so that the upper elastic ring 41 having the configuration and function similar to those of the detachable part is provided.

The detachable part 30 of the present invention allows the front cover part 20 to come into close contact with the abdomen of the body, the abdomen and the waist, and a portion of the back region of the waist, by binding the elastic ring 32 having a tie adjusting part 31 that may adjust a length in a tie to each of the left and right button parts 23 provided around the edges of both ends 21 of the front cover part 20. The detachable part 30 may be configured to mainly surround the back region of a user's waist and allow the front cover part to come into close contact with and be bound to his or her abdomen and waist.

Further, the detachable part 30 is an elastic material of a mainly single line, and has on left and right sides thereof the elastic rings 32. The detachable part may have the tie adjusting part 31 to simply adjust the size of the elastic ring 32 and the length of the detachable part 30 in the tie.

As illustrated in FIG. 1A, the left and right elastic rings 32 of the detachable part 30 further have two knots 31a, respectively, to prevent the elastic rings from being loosened when the elastic rings 32 are adjusted by the tie adjusting part 31. It is apparent to those skilled in the art that the detachable part is mainly made of an elastic material capable of adjusting the length of a string or a cord.

Further, referring to FIG. 1A, the binding part 33 is coupled to the left and right button parts 23 that are connected to both ends 21 of the front cover part 20, and the detachable part 30 on which the elastic ring 32 having the tie adjusting part 31 that may be adjusted in the tie is formed.

As illustrated in FIG. 1A, the left and right button parts 23 are provided on both ends 21 of the front cover part 20, and may be formed on both sides of the detachable part 30 in the shape of the elastic rings 32.

As illustrated in FIG. 1A, the elastic rings 32 of the detachable part 30 and the button parts 23 of both ends 21 of the front cover part 20 may be coupled to each other via the binding part 33. Of course, the button and the ring may be provided in locations opposite to the above-described locations, may include a hook and a ring for various purposes, or may be implemented by general detachable means (buttons, snaps, and magnets of various shapes).

One button is mainly attached to each of the left and right button parts 23 of both ends 21 of the front cover part. However, two buttons may be attached to each of the button parts depending on an application and a size. Further, a snap and a magnet may be provided on the left and right button parts 23 of both ends 21 of the front cover part to constitute a separate connecting ring.

Further, one of the left and right elastic rings of the detachable part 30 may be secured to one end of the front cover part 20 or may be formed as a fixing ring via a knot, while the elastic ring 32 having the tie adjusting part 31 that may be adjusted in the tie may be provided on an opposite end. That is, only one tie adjusting part may be provided instead of the left and right tie adjusting parts of the elastic rings.

Meanwhile, it is apparent to those skilled in the art that the tie adjusting part 31 of the elastic ring of the detachable part 30 may use any general means including a tie, a knot and others, as long as it is possible to adjust the length of a string or a cord. A user may always adjust the elastic ring of the detachable part to a desired length using the tie adjusting part or the knot, such that the user's abdomen wear fits for his or her waist size.

Further, the configuration and function of the left and right elastic rings of the detachable part 30 may be likewise applied to the upper and lower elastic rings 41 and 43 of the front cover part.

Figure 3:
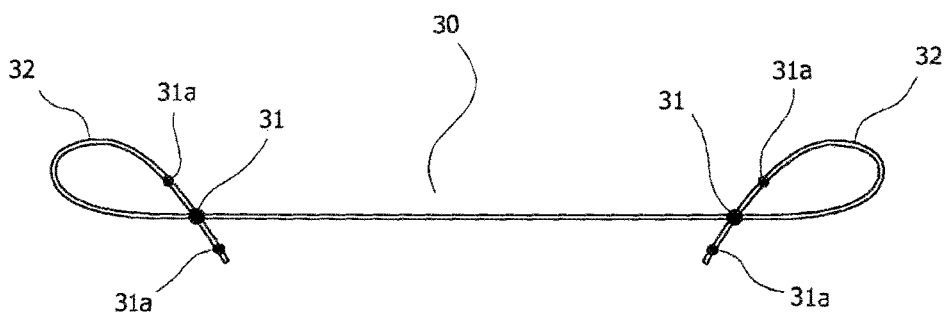
FIG. 3 is a view illustrating a detachable part included in a binding part of an abdomen wear according to an embodiment of the present invention.

Referring to FIG. 3, the configuration of the detachable part 30 included in the binding part 33 of the abdomen wear according to the embodiment of the present invention will be described in detail.

In FIG. 1A, the edge of each end 21 of the front cover part is formed at right angles, but may be rounded or protrude in a round shape. It is apparent to those skilled in the art that the patch or seam (see FIGS. 2A to 2C) that is one of various auxiliary parts 28 is provided on the edge of each end 21.

FIG. 1B is a front view of the abdomen wear. Here, both ends 21 of the front cover part 20 extend towards the left and right waist sides to cover sides or a portion of a back region of the waist.

Further, a trademark, a name, a patch, or various designs may be detachably attached to the front cover part or both ends thereof, but may be preferably attached to a front.

The upper elastic ring 41 may be provided with the button (or snap) 29 of the upper-end central portion 40 of the front cover part 20 to have the configuration and function similar to those of the detachable part. Since the adjustment is possible in the tie of the tie adjusting part 31 by connecting the button with the ring, a user may conveniently use the abdomen wear.

When a user puts on the abdomen wear according to the embodiment of the present invention, the upper elastic ring 41 is fitted over a button sewn on a shirt or upper clothing, a necklace or the like to cause the front cover part 20 to come into close contact with the abdomen and to prevent the front cover part 20 from sagging or being folded down. Meanwhile, a woman may fit the upper elastic ring 41 over a button attached to a brassiere, thus allowing the front cover part 20 to come into close contact with the abdomen even when she puts on upper clothing having no button.

The upper elastic ring of the abdomen wear according to the embodiment of the present invention is applied similarly to the configuration and function of the detachable part 30. Thus, since it is easy to adjust the length of the upper elastic ring 41 via the tie adjusting part 31 included in the upper elastic ring 41, it is advantageous in that the upper elastic ring 41 is coupled to the button of the upper clothing, the necklace or the like to allow the front cover part 20 to come into close contact with the abdomen.

Referring to FIG. 1B, vertical patches that are one of various auxiliary parts 28 formed of an elastic material or a non-elastic material may be further provided on left and right sides around the edges of both ends 21 and the front cover part 20. In order to enhance the aesthetic effect, various auxiliary parts 28 may take the shape of a lace, a bias, a patch, a decoration, etc. Particularly in the case where the abdomen wear is applied to outer clothing, various designs or metal decorations may be partially formed on the front cover part and various auxiliary parts.

The textile patch or seam extends on inner sides, mainly outer sides of both ends 21 of the front cover part to adjust the looseness of the front cover part. The patch or seam serves to reduce the elasticity of the knit after a user puts on the abdomen wear, displays a brand and colors, and makes it easy to be distinguished after washing, thus solving the above-described problems. Since the abdomen wear is mainly underwear, it is made of organic cotton, silk, natural and functional fiber and is produced by cutting the single-layered, particularly the two-layered knit on the bias. Of course, it is apparent to those skilled in the art that the abdomen wear is made of fiber, such as a mesh or hemp that is cool enough to wear as underwear or outer clothing in summer.

FIG. 1C is a real-view of the abdomen wear. Openings 26 are formed between covering 25 and lining 24 of the two-layered front cover part 20 to be located on left and right sides thereof, thus forming 26a a pocket therein and thereby allowing the separate liner 51 (see FIG. 4) to be attached therein. In order to detachably attach the separate liner 51, liner attachments 50 may be formed on an inside of the lining 24 of the front cover part using a Velcro® tape (hook-and-look fastener) loop.

An edge of the lining 24 that is open by the opening 26 may be finished by main sewing, special sewing, a lace for providing aesthetic effect, etc. similarly to the edge of the front cover part.

Referring to FIG. 1C, four Velcro® tape (hook-and-look fastener) loops may be formed at predetermined intervals on upper, lower, left and right sides to correspond to the liner attachments 50 and allow the separate liner 51 to be attached to upper, lower, left and right sides on the inside of the lining 24 in the two-layered front cover part 20. Of course, one or more loops may be provided depending on the size of the front cover part.

The front cover part 20 provided on the abdomen wear according to the embodiment of the present invention may be changed in various shapes.

As an example, the abdomen wear according to the embodiment of the present invention may directly or indirectly extend the lower end of the front cover part downwards. The downward extension of the front cover part allows it to cover the abdomen even when a user sleeps without a blanket in hot summer. A lower extension (not shown) of the front cover part 20 may be mainly composed of single-layered knit.

As another example, the abdomen wear according to the embodiment of the present invention may extend the upper end of the front cover part 20 towards the chest. This solves a problem in which the upper elastic ring becomes long so as to couple the upper elastic ring to a button of clothes in the case of putting on a T-shirt or a running shirt. The abdomen wear may extend wide or long towards the chest depending on a required purpose.

Further, a brassiere may be formed for a woman on an upper extension of the front cover part 20, and chest covers may be provided for male and female chest regions. A detachable part as a second binding part may be provided to allow the brassiere or the chest cover to come into close contact with the chest.

As a further example, the abdomen wear according to the embodiment of the present invention may extend both the upper and lower ends of the front cover part 20 long. An abdomen region of the front cover part 20 may be formed in two layers, and the lower extension and the upper extension may be formed in one layer. It is possible to use one layer and two layers in combination.

Meanwhile, in the abdomen wear according to the embodiment of the present invention, the front cover part may be formed by cutting mainly a knit on the bias, and the front cover part may be designed to be manually, semi-automatically or automatically knitted using bias-cutting, and the front cover part may be produced by cutting knitted fabric, such as organic cotton or silk, on the bias. According to an intended purpose, it may be formed in one layer or two layers using a knit, woven textile, or leather. One layer and two layers may be used in combination to fit for the purpose. The front cover part 20 may be formed of mainly a knit, woven textile, leather, or a padded material in one layer, a combination of one layer and two layers, and two layers, and may be entirely or partially formed of materials, such as natural dyeing, medicinal herb, artificial diamond, jewelry including gold and silver, and mineral, which keep the body warm, aid blood circulation, and are beneficial for health, in combination in one layer or two or more layers, may be manufactured by manual labor or a sewing machine to have embroidery, five colors, or piece fiber and maximize heat insulating effect, adhesion and aesthetic effect, and may be manufactured using traditional Korean paper, silk, five colored yarn, gold and silver yarn, and gold and silver foils in combination, thus consequently being capable of creating a new luxury craft.

The abdomen wear according to the embodiment of the present invention may be used as outer clothing as well as underwear. For example, when the abdomen wear is used as the outer clothing, a whole portion or a central portion of the covering of the front cover part 20 may be made of leather, and other portions may be made of fiber. In this case, the lining may be fiber. Both the leather and the fiber may be employed for respective parts according to an intended purpose.

Further, in order to stylishly cover the navel of a young woman in summer, a mesh of fiber may be employed in one layer or in both one layer and two layers to provide various designs and decoration, thus achieving stylish effect and keeping a navel region warm.

The abdomen wear according to the embodiment of the present invention may have on a front or a back thereof one or more separate pockets to allow a user's smartphone, passport or the like to be inserted therein.

If a user puts on the abdomen wear such that the front cover part is disposed on the back region of the waist and the detachable part is disposed on the abdomen, it is possible to keep the back region of the waist warm.

Further, the exterior of the front cover part of the abdomen wear according to the embodiment of the present invention may be manufactured to be slightly swollen, so that a pack filled with brown rice, five grains, seeds, germanium, jade and others as the separate liner forms the pocket of the front cover part or is put into the pocket while remaining unheated or being heated. In this state, when a user puts on the abdomen wear in a daily life or at bedtime, it is possible to apply heat to the abdomen.

The separate liner 51 of the abdomen wear according to the embodiment of the present invention will be described in detail with reference to FIG. 4.

Figure 2A:
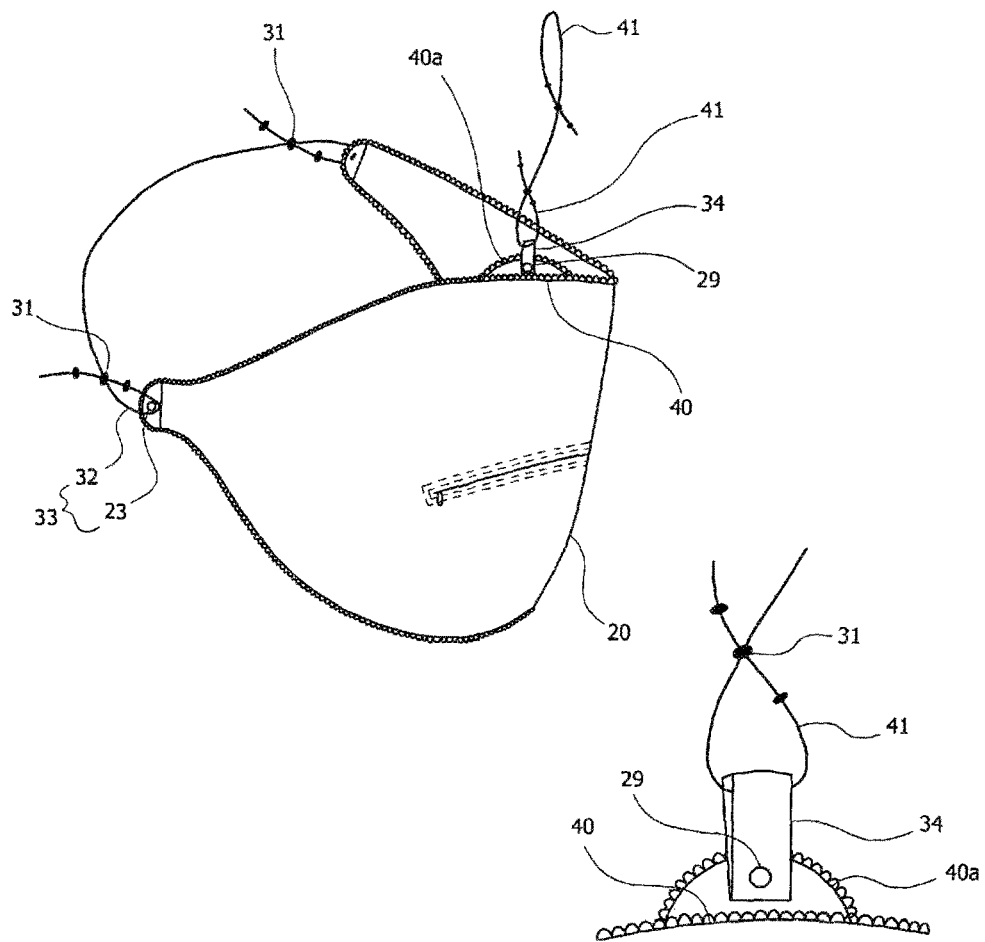
FIGS. 2A to 2C are a perspective view (FIG. 2A) illustrating a second abdomen wear according to an embodiment of the present invention, and a front view (FIG. 2B) and a rear view (FIG. 2C) of a front cover part.
Figure 2B:
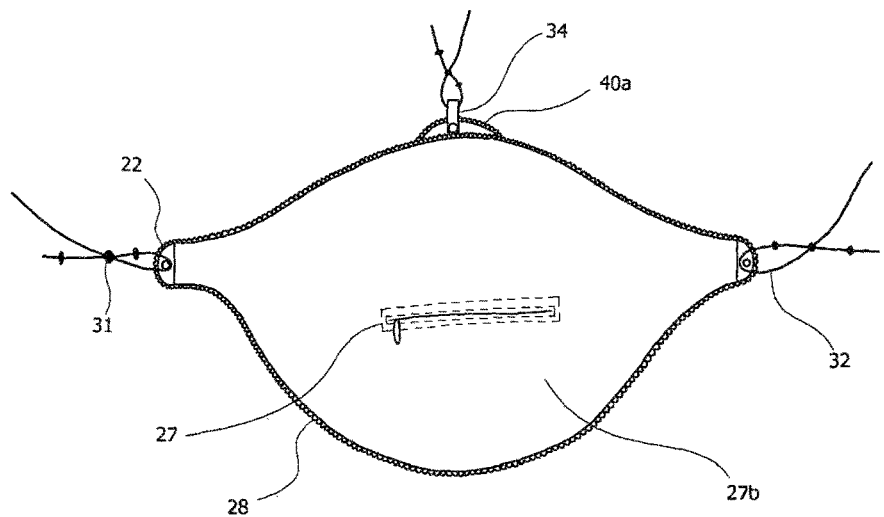
Figure 2C:
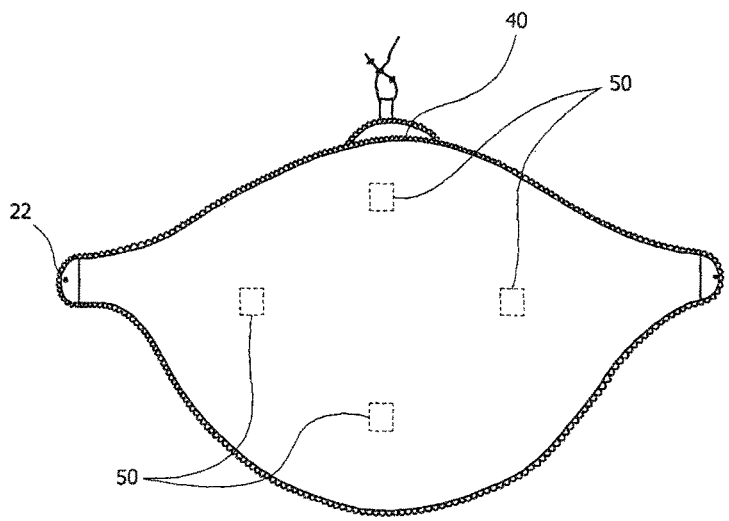

FIGS. 2A to 2C are a perspective view (FIG. 2A) illustrating an abdomen wear according to a second embodiment of the present invention, and a front view (FIG. 2B) and a rear view (FIG. 2C) of a front cover part. The abdomen wear of FIGS. 2A to 2C may include a zipper 27 that is provided on a central portion of a front of the front cover part 20, and a pocket 27b that is coupled with the zipper and is defined in the front cover part 20.

The pocket may be formed by the following methods: the pocket may be formed by sewing a portion immediately above the lower end of the front cover part 20 in two layers, the pocket 27b may be formed by vertically sewing a predetermined portion of the left and right sides of the front cover part, and the pocket 27b may be formed by making left and right sides in one layer except for a pocket forming portion. According to various shapes of pockets, the zipper 27 may be opened or closed to put or take the separate liner 51 that is the second lining into or from the pocket.

Referring to FIGS. 2A to 2C, seam parts 22 are further provided on both ends 21 of the front cover part, and left and right button parts 23 are provided on the seam parts 22. The seam parts 22 on both ends are mainly made of textile to improve adhesion, aesthetic effect, and distinguishability. Various auxiliary parts 28 may be naturally provided on edges of the seam parts.

Further, FIGS. 2A to 2C show a case where the length of both ends 21 of the front cover part 20 and the seam parts 22 of both ends is short to mainly cover a front region of the abdomen. This length is about ½ or less of the entire waist circumference, and the length of the detachable part 30 may be set such that it covers about ½ or more of the entire waist circumference. Of course, the length of both ends 21 of the front cover part 20 and the seam parts 22 of both ends may be set such that they extend to the back region of the waist and cover about ½ or more of the entire waist circumference, and the detachable part may cover ½ or less of the entire waist circumference (see FIGS. 1A to 1C).

Meanwhile, referring to FIG. 2A, the upper elastic ring 41 may have the snap (or button) 29 on a seam part 40a of the upper-end central portion 40 of the front cover part 20, and a separate connecting ring 34 may be further provided via the snap, the button or the like. The upper elastic ring 41 may be formed by applying the configuration and function of the detachable part 30 having the tie adjusting part that may be adjusted in the tie.

The lower elastic ring (not shown) may be further provided. The lower elastic ring has a button on the lower-end central portion (not shown) of the front cover part 20 or on the seam part (not shown) of the lower-end central portion so that the elastic ring 43 (not shown) may be provided on the lower end.

The lower elastic ring is fastened to a button of a man's underwear, and a lower portion of the front cover part extends to cover a lower abdomen. Recently, since much men's underwear has buttons, the abdomen wear may further come into close contact with the abdomen and may be prevented from being possibly folded when the abdomen wear is put on together with the above-described underwear having the button. Since other configurations remain the same as FIGS. 1A to 1C, they will not be described in detail.

Thus, it is apparent to those skilled in the art that both ends 21 of the front cover part, the seam parts 22 on both ends, the upper and lower-end central portions, and the seam parts are provided with the buttons or snaps, and then various second connecting rings are provided if necessary in terms of a function and aesthetic effect.

As shown in FIGS. 2A to 2C, the snap (or button) 29 may also be attached to the seam part 40a of the upper-end central portion of the front cover part. This may be connected with a separate connecting ring 34, and the separate connecting ring 34 may be implemented as general opening means, for example, a button, a snap, a magnet, an additional ring and the like.

Although the front cover part configured as such has been described in detail with reference to the accompanying drawings, it is apparent to those skilled in the art that the configurations of FIGS. 1A to 1C and FIGS. 2A to 2C may be combined with each other.

Even when the front cover part is one layer, a combination of one layer and two layers, and two layers, it is apparent to those skilled in the art that it may be variously manufactured with a knit, knitted fabric, or woven textile based on the description of FIGS. 1A to 1C and FIGS. 2A to 2C.

FIG. 3 is a view illustrating the detachable part 30 included in the binding part 33 of an abdomen wear according to an embodiment of the present invention.

Since the detachable part 30 of the binding part 33 shown in FIG. 3 has been described with reference to FIGS. 1A to 1C, a detailed description thereof will be omitted herein. In addition, when the elastic ring of the detachable part formed of an elastic material of a single line is adjusted by the tie adjusting part 31 that adjusts a length in the tie, it is possible to prevent the elastic ring 32 from being loosened or blocked by forming the knot 31a that has a control function inside or outside the elastic ring.

It is apparent to those skilled in the art that the elastic ring 32 of the detachable part 30 of FIG. 3 may be employed on upper and lower locations instead of left and right sides, by applying similar configuration and function to the elastic ring 41 provided on the upper-end central portion of the front cover part or the seam part of the upper-end central portion, and the elastic ring 43 provided on the lower-end central portion and the seam part of the lower-end central portion.

Referring to FIGS. 1A to 1C and FIGS. 2A to 2C, the abdomen wear may have the openings 26 on both sides of the pocket that is formed 26a on the lining 24 of the two-layered front cover part 20 that is made by cutting mainly a knit on the bias, or may have the zipper 27 and the pocket 27b, with the liner attachments 50 being provided on the lining 24.

One or more liner attachments 50 may be provided on the central portion of the upper end, the left and right sides of the upper end of the lining 24 of the front cover part. The number and position of liner attachments may be adjusted as desired. Preferably, a total of four Velcro® tape (hook-and-look fastener) loops may be formed on upper, lower, left and right sides and then the separate liner 51 may be attached. That is, after a user opens the opening 26 of the front cover part 20 or the zipper 27, the separate liner is inserted into the two-layered structure or the pocket, the liner attachments 50 and the attachments 55 of the separate liner are attached to each other, so that it is possible to secure the separate liner 51 to the interior of the front cover part 20 or the pocket.

Such a configuration prevents the separate liner 51 from slipping down or moving leftwards or downwards in the two-layered structure or the pocket, thus always keeping the abdomen warm.

The attachment 55 provided on the separate liner 51 may also be formed using the Velcro® tape (hook-and-look fastener) hook 52 or the like. Since the abdomen wear according to the embodiment of the present invention uses the Velcro® tape (hook-and-look fastener) or the button as the liner attachment 50 and the attachment 55 of the separate liner, it is possible to separate the separate liner and the front cover part from each other when it is required to wash the abdomen wear according to the embodiment of the present invention. Further, the position of the liner attachment may be appropriately changed depending on the size and the purpose of the separate liner, and the separate liner 51 may be doubly provided around upper, lower, left and right edges.

Figure 4:
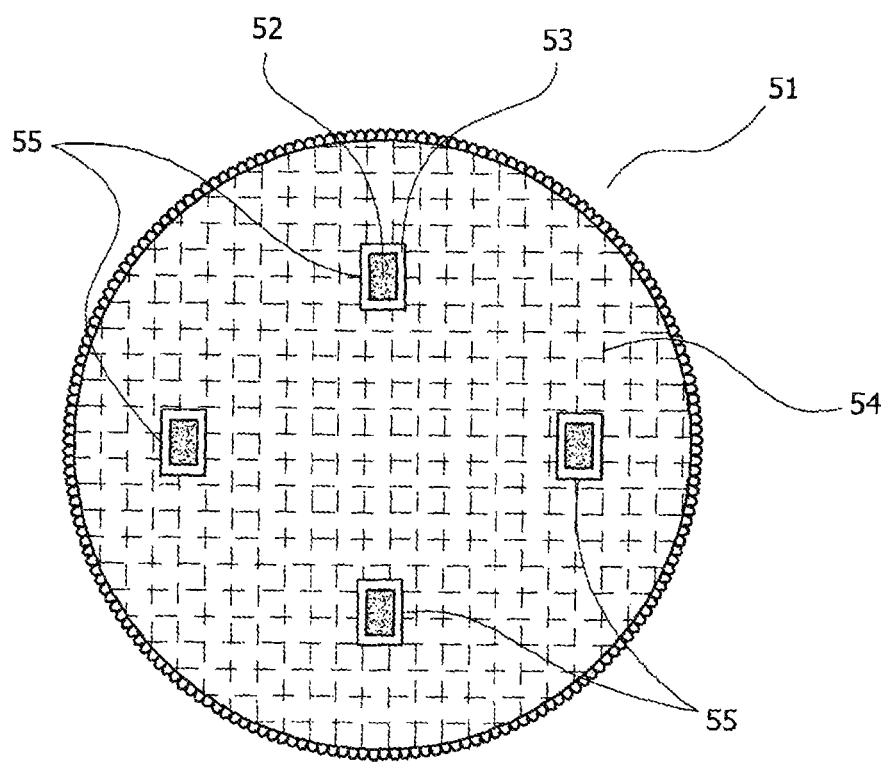
FIG. 4 is a view illustrating a separate liner of an abdomen wear according to an embodiment of the present invention.

FIG. 4 is a view illustrating the separate liner 51 of the abdomen wear according to an embodiment of the present invention. Referring to FIG. 4, the attachment 55 of the separate liner and wormwood cotton padded with gauze or fiber may be included. The attachment may be attached to the liner attachment 50 of the abdomen wear according to the embodiment of the present invention. The separate liner 51 is formed of various materials that are beneficial for the body, for example, wormwood cotton 54 padded with knitted gauze or fiber, padded mugwort cotton, animal or vegetable padded cotton, existing cotton, natural and functional fiber, leather, etc. to keep the abdomen warm depending on an intended purpose. The separate liner may be made in one layer or two layers using both cotton and fiber. A middle portion and a lower end of the separate liner may be formed thick.

As an example, an inner side may be made of padded wormwood cotton and an outer side may be made of leather to enhance heat insulating effect, so that it is possible to use the abdomen wear even in midwinter or the intense cold. When it is desired to use the abdomen wear in summer, the separate liner may be made of rayon, hemp, ramie fabric or the like to allow a user to feel cool, in addition to enhancing the heat insulating effect.

Further, fiber of the Velcro® tape (hook-and-look fastener) auxiliary part 53 may be attached to the hook of the separate liner 51 and the loop of the liner attachment 50 of the front cover part, as a support.

Although it has been described in the above embodiment that the abdomen wear according to the embodiment of the present invention has one separate liner 52 to keep the abdomen warm, the abdomen wear according to the embodiment of the present invention may have liners that are adjusted in volume and interval of padded materials and in size depending on an intended season or purpose, for example the purpose for keeping the lower part of the abdomen warm. The separate liner 51 may be made of substances that are beneficial for the body, for example, artificial diamond, jewelry, mineral, medicinal herb, grains, and seeds, which have energy, by mixture or for decoration.

Meanwhile, plants, far-infrared radiation, mineral, leather, herb using natural, artificial and functional fiber, and energy generating substances, which are beneficial for the body, are coupled to the front cover part 20, both ends 21, the seam parts 22 on both ends, the left and right button parts 23, the detachable part 30, and the separate liner 51, thus keeping the abdomen warm and promoting health.

The button may likewise have various shapes and functions using natural nacre, magnets, jewelry and the like.

Hereinafter, a method of putting on the abdomen wear according to the embodiment of the present invention will be described. First, a user fastens the elastic ring 32 provided on an end of the detachable part 30 to the button part 23 provided on a side of the front cover part, adjusts the tie of the tie adjusting part 31, or wind the elastic ring around the button once. The front cover part 20 is located on an abdomen region, the detachable part 30 surrounds the back region of the waist, the tie adjusting part 31 of the elastic ring 32 provided on an opposite side is adjusted using the opposite button part 23, so that the abdomen wear is adjusted to fit for his or her waist circumference, and then the elastic ring is fastened to or surrounded around the button once.

At this time, the seam parts 22 of both ends of the front cover part 20 are placed on the soft skin before left and right sides of the abdomen (see FIGS. 2A to 2C), and both ends 21 of the front cover part are placed on the soft skin behind the sides (see FIGS. 1A to 1C). Subsequently, in the case of fastening the upper elastic ring 41, the elastic ring having the configuration and function similar to those of the detachable part 30 is fastened to the button (or snap) 29 of the upper-end central portion of the front cover part and is adjusted by the tie adjusting part. Then, the upper elastic ring 41 is fitted over a button of a user's upper clothing and is adjusted in length by the tie adjusting part. In this state, he or she fastens the button of the upper clothing.

If the seam parts of both ends are snaps, a separate connecting ring 34 equipped with a snap or a button may be used. In the case of a woman, the upper elastic ring may be fitted over a button that may be provided on a center of a brassiere.

Further, in the case of wearing the separate liner 51 that is the second lining, the front cover part 20 is turned inside out and then the separate liner is attached before the abdomen wear is put on. Alternatively, the front cover part 20 is placed on a flat surface, the openings 26 provided on the left and right sides of the front cover part 20 or the zipper 27 provided on the front thereof is opened, and the attachments 55 provided on the separate liner 51 are attached to the liner attachments 50 provided on the inside of the lining, and the separate liner is smoothed out by a user's hand. Then, this may be shaken out and worn, or may be zipped, shaken out and worn. Of course, after the abdomen wear is put on, the separate liner may be worn via the openings or the zipper.

Meanwhile, in the case of a man's underwear having a button, the lower elastic ring 43 may be fitted over the button to keep a lower portion of the front cover part flat.

While the present invention has been described with respect to the specific embodiments, it will be apparent to those skilled in the art that various changes and modifications may be made without departing from the spirit and scope of the invention as defined in the following claims.

[Description of Reference numerals]

| | |
|---|---|
| 20: front cover part | 21: both ends |
| 22: seam parts of both ends | |
| 23: left and right button parts | |
| 24: lining | 25: covering |
| 26: opening | |
| 26a: formation of pocket shape | |
| 27: zipper | 27b: pocket |
| 28: various auxiliary parts | 29: button or snap |
| 30: detachable part | 31: tie adjusting part |
| 31a: knot | 32: elastic ring |
| 33: binding part | 34: separate connecting ring |
| 40: upper-end central portion | |
| 40a: seam part of upper-end central portion | |
| 41: upper elastic ring | |
| 43: lower elastic ring | 50: liner attachment |
| 51: separate liner | |
| 52: Velcro ® tape (hook-and-look fastener) tape hook | |
| 53: Velcro ® tape (hook-and-look fastener) tape auxiliary part | |
| 54: padded wormwood cotton | |
| 55: attachment of separate liner | |

The invention claimed is:

1. An abdomen wear comprising:
a front cover part (20) formed of a single-layered or a two-layered knit cut on bias to cover an abdomen of a body, wherein the front cover part (20) comprises two ends (21), seam parts (22) provided at both ends, and left and right button parts (23) configured to cause the front cover part to come into close contact with the abdomen of the body;
a binding part (33) including a detachable part (30) having an elastic ring (32) on which a tie adjusting part (31) is formed, the tie adjusting part being adjustable in a length of tying, so that the left or right button part (23) engages the elastic ring (32) through the binding part (33); and
an upper elastic ring (41) having a button or a snap (29) on an upper-end central portion (40) of the front cover part or a seam part (40a) of the upper-end central portion, and having another tie adjusting part (31) that is adjustable in a length of tying.

2. The abdomen wear of claim 1, wherein openings (26) are provided on portions of left and right sides of the front cover part (20) formed in two layers, thus forming (26a) a pocket shape therein, or a zipper (27) is provided on a central portion of a front of the front cover part, thus forming a pocket (27b), and a liner attachment (50) is formed on a surface therein to allow a separate liner (51) to be attached thereto.

3. The abdomen wear of claim 1, wherein the front cover part (20) is located at an intermediate position of an entire waist circumference to cover a half or more of the entire waist circumference, and the detachable part (30) covers a half or less of the entire waist circumference.

4. The abdomen wear of claim 2, wherein the separate liner (51) is further provided and attached inside the front cover part, the attached separate liner (51) is selected from a group consisting of padded wormwood cotton, padded mugwort cotton, padded medicinal herb cotton, padded herb cotton, padded vegetable cotton, padded silk cotton, padded wool cotton, fiber, and leather, and an attachment (55) of the separate liner further comprises a hook-and-loop fastener hook (52) and a hook-and-loop fastener auxiliary part (53).

5. The abdomen wear of claim 1, wherein the front cover part, the two ends (21), the seam parts of the two ends and an upper end, and a predetermined portion and an edge of a separate liner (51) further comprise auxiliary parts (28)

including lace, bias, patch or decoration, so as to improve aesthetic effect, adhesion and elasticity.

* * * * *